Feb. 14, 1939. E. C. GEIGER Plant Pat. 313
CHRYSANTHEMUM
Filed Jan. 13, 1938
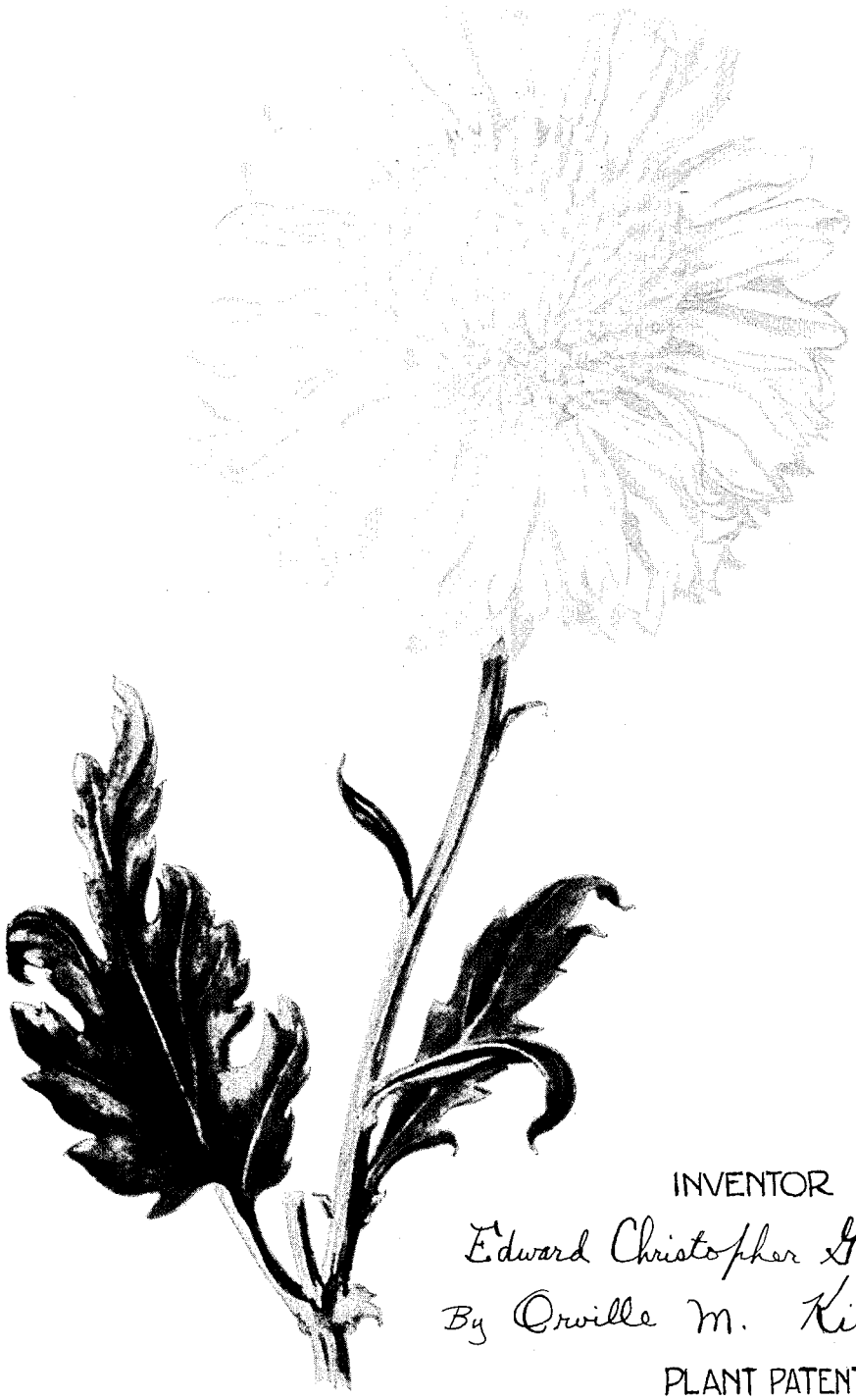
INVENTOR
Edward Christopher Geiger
By Orville M. Kile
PLANT PATENT AGENT Patented Feb. 14, 1939

Plant Pat. 313

UNITED STATES PATENT OFFICE

313

CHRYSANTHEMUM

Edward Christopher Geiger, North Wales, Pa., assignor to Wm. A. Geiger and Sons, Inc., North Wales, Pa.

Application January 13, 1938, Serial No. 184,883

1 Claim. (Cl. 47—60)

My present discovery relates to improvements in chrysanthemums of the anemone type and is a sport of the variety known as Long Island Beauty, having been discovered as a single branch on a plant otherwise pink-flowered. The pink-flowered branches were cut away and the white flowered branch developed. Cuttings were taken from this branch and propagated through several generations, the qualities of the variety proving to be permanent.

This new variety resembles its parent in many respects, the chief differences being in color and form. The petals (or ray flowers) of the present variety are pure white and extend horizontally from the cushion, while the petals of its parent are pink and have considerably more tendency to droop backward from the cushion. The horizontal arrangement of petals gives the effect of a much larger flower.

The original illustration shows a fully-opened blossom of this new variety, together with some of the stem and foliage.

Following is a more complete description of this new variety. Color plate references are to Ridgway's Color Standards and Nomenclature.

Growth habits:

Vigorous growth. Tall, but varying according to circumstances. If pinched in July, it attains a height of four feet. Highly productive and prolific. Propagates freely. Has relatively high percentage of perfect flowers as compared to other varieties.

Bloming habits:

If pinched and disbudded, the blossoms are essentially as herein shown and described and the plants produce an average of four blooms each. However, the same variety may be left to grow as a pompon chrysanthemum if no pinching or disbudding is done, in which case the blossoms are proportionately smaller. Number of blooms to be grown on each plant is optional, that is, any number may be selected.

Blooming period:

Thanksgiving or later.

Disease resistance:

Exceedingly resistant to disease.

Blossoms:

Consist of large cushion surrounded by multiple fringe of petals (or ray flowers).

*Size.*—Averages five inches across.

*Cushion.*—The cushion consists of numerous tubular florets (about 350), averaging slightly more than an inch in length. The greater part of the length of these florets is white although they have touches of green and yellow. The lower end (attached to the cushion base) is green for about one-eighth inch, then comes a stripe of yellow about half as wide. After this is the white portion which is tipped with Lemon Chrome (Plate IV) in the prime stage and is slightly darker when first opened. Because these florets are bunched so closely together, none of the white is evident at a glance and the general effect is of a solid cushion of Lemon Chrome color.

*Cushion base.*—The cushion base to which the florets are attached is a green, dome-like, pithy structure about one-half inch across.

*Petals (or ray flowers).*—Average about 150 petals (or ray flowers) per blossom. They are pure white and extend horizontally from the cushion, that is, in a plane parallel to that of the cushion. These petals do not curve backward as do those of the parent variety blossom. Length of petals, 2 to 2¼ inches. Attached under the cushion, to the cushion base, the florets extend 1½ to 2 inches beyond the edge of the cushion.

*Bracts.*—About 30 closely overlapping bracts forming the involucre. Green with brown, membranous edge all around.

*Foliage.*—Abundant. Empire Green (Plate XXXII). Leaves—large and of heavy substance.

*Stems.*—Strong and rigid. Brittle. Pithy within, ribbed on surface. Of practically the same color as the foliage. Slightly stronger growth than the stems of the parent plant.

Having thus disclosed my discovery, I claim:

The new and distinct variety of chrysanthemum plant as herein shown and described, characterized particularly by its prolific production of large percentage of perfect blooms having very large cushion of Lemon Yellow, edged with petals of pure white arranged perpendicular to the stem.

EDWARD CHRISTOPHER GEIGER.